US010074255B2

(12) United States Patent
Prabhakar et al.

(10) Patent No.: US 10,074,255 B2
(45) Date of Patent: Sep. 11, 2018

(54) UNSAFE WORK CONDITION TEMPERATURE ALERTS IN PORTABLE GAS DETECTORS

(71) Applicant: Fluke Corporation, Everett, WA (US)

(72) Inventors: Dileepa Prabhakar, Mill Creek, WA (US); Christopher Corrigan, Seattle, WA (US); Pronitha Shankarananda, Bellevue, WA (US); Joel Andrew Hartel, Mukilteo, WA (US); Dominic A. Ivankovich, Everett, WA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 15/365,639

(22) Filed: Nov. 30, 2016

(65) Prior Publication Data
US 2017/0154509 A1 Jun. 1, 2017

Related U.S. Application Data

(60) Provisional application No. 62/261,215, filed on Nov. 30, 2015.

(51) Int. Cl.
*G08B 17/00* (2006.01)
*G08B 17/06* (2006.01)
(Continued)

(52) U.S. Cl.
CPC ............ *G08B 17/06* (2013.01); *G01K 1/024* (2013.01); *G01K 3/005* (2013.01);
(Continued)

(58) Field of Classification Search
CPC ........ G08B 21/16; G08B 25/10; G08B 17/06; G01K 1/024; G01K 3/005; G01N 33/0075
(Continued)

(56) References Cited

U.S. PATENT DOCUMENTS

| 4,258,002 A * | 3/1981 | Barr | G01N 27/16 422/95 |
|---|---|---|---|
| 7,263,379 B1 * | 8/2007 | Parkulo | G08B 21/02 340/501 |

(Continued)

FOREIGN PATENT DOCUMENTS

| JP | 2011-107964 A | 6/2011 |
|---|---|---|
| WO | 2013/116933 A1 | 8/2013 |
| WO | 2015/054288 A1 | 4/2015 |

OTHER PUBLICATIONS

Partial European Search Report for Application No. EP 16 20 1438 dated May 12, 2017, 17 pages.
(Continued)

*Primary Examiner* — Zhen Y Wu
(74) *Attorney, Agent, or Firm* — Seed Intellectual Property Law Group LLP

(57) ABSTRACT

A gas detector includes environmental condition detection circuitry that includes one or more sensors, data processing circuitry, and wireless communication circuitry. The gas detector is configured to be carried by a user. The environmental condition detection circuitry detects the presence or lack of presence of a particular gas in a vicinity of the gas detector and further detects a temperature in the vicinity of the gas detector and communicates detection data to the data processing circuitry. In response to detection of a hazardous temperature condition, the data processing circuitry of the gas detector provides an alert notification to the user carrying the gas detector. Also disclosed is an alert system including multiple gas detectors in which a first gas detector communicates an alert to a second gas detector via wireless communication, and in response, the second gas detector transmits the alert to another gas detector or device via wireless communication.

20 Claims, 5 Drawing Sheets

(51) Int. Cl.
*G08B 21/16* (2006.01)
*G08B 25/10* (2006.01)
*G01K 1/02* (2006.01)
*G01K 3/00* (2006.01)
*G01N 33/00* (2006.01)

(52) U.S. Cl.
CPC ......... *G01N 33/0075* (2013.01); *G08B 21/16* (2013.01); *G08B 25/10* (2013.01)

(58) Field of Classification Search
USPC ....................................................... 340/584
See application file for complete search history.

(56) References Cited

U.S. PATENT DOCUMENTS

| | | | |
|---|---|---|---|
| 8,330,605 B2 | 12/2012 | Johnson, Jr. et al. | |
| 8,400,317 B2 | 3/2013 | Johnson, Jr. et al. | |
| 2002/0101247 A1* | 8/2002 | Whynall | G01N 33/0018 324/460 |
| 2002/0142478 A1* | 10/2002 | Wado | G01N 27/124 436/151 |
| 2004/0004547 A1* | 1/2004 | Appelt | G08B 21/02 340/573.1 |
| 2009/0136885 A1* | 5/2009 | Manno | B27H 5/08 432/37 |
| 2010/0063748 A1* | 3/2010 | Mottier | G01N 21/3504 702/24 |
| 2011/0259080 A1* | 10/2011 | Ratcliffe | G01N 27/12 73/23.35 |
| 2012/0169289 A1* | 7/2012 | Kim | H01M 2/105 320/134 |
| 2012/0269194 A1 | 10/2012 | Kobayashi et al. | |
| 2012/0280818 A1* | 11/2012 | Johnson, Jr. | H04W 4/043 340/632 |
| 2013/0102257 A1* | 4/2013 | Bedi | H04W 4/023 455/66.1 |
| 2013/0209315 A1* | 8/2013 | Kimura | G01N 25/4826 422/88 |
| 2014/0028829 A1 | 1/2014 | Kieffer et al. | |
| 2015/0075256 A1* | 3/2015 | Basham | G01N 33/0016 73/31.01 |
| 2016/0081415 A1* | 3/2016 | Handshaw | A42B 3/046 2/5 |
| 2016/0109495 A1* | 4/2016 | Sterkel | G06F 17/212 702/62 |
| 2016/0119739 A1* | 4/2016 | Hampel | H04W 4/70 370/315 |

OTHER PUBLICATIONS

Accenture Plant and Commercial Services, "Helping Achieve High Performance Safety using Intelligent Industrial Mobility" Copyright© 2013 Accenture, 8 pages.

Bleiberg, J. et al., "Three Ways Mesh Networks with Peer-to-Peer Connections Can Revolutionize Communications (without the Internet)", Apr. 25, 2014, 4 pages.

Extended European Search Report, dated Feb. 24, 2017, for European Application No. 16201517.6-1555, 9 pages.

* cited by examiner

UNSAFE WORK CONDITION TEMPERATURE ALERTS IN PORTABLE GAS DETECTORS

BACKGROUND

Technical Field

This disclosure pertains to detection systems, and particularly to systems that generate alerts based on detected temperature.

Description of the Related Art

Portable gas detectors are used as personal safety tools to detect the lack of certain gases such as oxygen, or to detect the presence of certain dangerous gases, such as combustible or toxic gases. Gas detectors may be used for spot testing of leaks or for use in confined spaces and for other portable/personal use in hazardous environments. Portable gas detectors may be configured, for example, as a hand-held, clip-on, or wearable devices, and include all types of single-gas and multi-gas detectors.

In a confined space, working conditions are typically difficult and dangerous. Portable gas detectors help ensure that the user is alerted to unsafe conditions of gas levels.

However, current known gas detectors are not configured to measure temperature of the environment around the gas detector. Ambient temperatures (and possibly body temperatures) may become quite high because of location (especially in confined spaces) and layers of safety gear worn by users of the gas detectors. Such temperatures can be debilitating or fatal if the temperature is high enough for sustained periods of time of continuous work in such environments. In other situations, the temperature of working conditions may be too low for sustained periods of time of continuous work.

The present disclosure provides solutions to deficiencies and drawbacks in current gas detection systems.

BRIEF SUMMARY

In various embodiments, a gas detector of the present disclosure includes environmental condition detection circuitry, data processing circuitry, and wireless communication circuitry. The environmental condition detection circuitry includes one or more sensors that detect the presence or lack of presence of a particular gas in a vicinity of the gas detector. Furthermore, the gas detector is configured to be carried by a user. The environmental condition detection circuitry also includes one or more sensors that detect a temperature in the vicinity of the gas detector and communicates temperature detection data to the data processing circuitry. In response to detection of a hazardous temperature condition, the data processing circuitry of the gas detector provides an alert notification to the user carrying the gas detector.

At least one of the one or more temperature sensors may be a biometric sensor configured to detect a body temperature of the user carrying the gas detector. Additionally or alternatively, at least one of the one or more temperature sensors may detect an ambient temperature in the vicinity of the gas detector. The data processing circuitry may detect a hazardous temperature condition when at least one of a body temperature of the user carrying the gas detector or an ambient temperature in the vicinity of the gas detector is beyond an upper and/or lower temperature limit. In further embodiments, the data processing circuitry may detect a hazardous temperature condition when at least one of a body temperature of the user carrying the gas detector or an ambient temperature in the vicinity of the gas detector is beyond the upper and/or lower temperature limit for a period of time beyond a time limit. The time limit may vary depending on a magnitude of at least one of the detected body temperature of the user or the ambient temperature. Furthermore, a sensory output of the alert notification provided to the user may vary depending on an amount of time beyond the time limit in which the detected body temperature of the user or the ambient temperature is beyond the upper and/or lower temperature limit. The environmental condition detection circuitry may also include one or more humidity sensors that detect a humidity in the vicinity of the gas detector, and the time limit may vary depending on a magnitude of the detected humidity.

In various embodiments, the upper and/or lower temperature limit for the user's body temperature may be different than the upper and/or lower temperature limit for the ambient temperature. A sensory output of the alert notification provided to the user may vary depending on an amount of temperature by which the detected body temperature of the user or the ambient temperature is beyond the upper and/or lower temperature limit. The environmental condition detection circuitry may further include one or more humidity sensors that detect a humidity in the vicinity of the gas detector, and the upper and/or lower temperature limit may vary depending on a magnitude of the detected humidity.

In various embodiments, an alert system may include a first gas detector as described above, wherein the first gas detector is configured to be carried by a first user, and a second gas detector as described above, wherein the second gas detector is configured to be carried by a second user. In response to detection of a hazardous temperature condition by the first gas detector, the data processing circuitry of the first gas detector may provide an alert notification to the first user and communicate the alert to the second gas detector via the wireless communication circuitry of the first gas detector. In response to receipt of an alert from the first gas detector, the data processing circuitry of the second gas detector may transmit the alert to another gas detector or device via the wireless communication circuitry of the second gas detector.

In various embodiments, in response to detection of a hazardous temperature condition by the second gas detector, the data processing circuitry of the second gas detector may provide an alert notification to the second user and communicate the alert to the first gas detector via the wireless communication circuitry of the second gas detector. In response to receipt of an alert from the second gas detector, the data processing circuitry of the first gas detector may transmit the alert to another gas detector or device via the wireless communication circuitry of the first gas detector.

The first gas detector may broadcast the alert in an ad hoc communication to the second gas detector without knowing that the second gas detector is in transmission range of the first gas detector. Likewise, the second gas detector may broadcast the alert in an ad hoc communication to the first gas detector without knowing that the first gas detector is in transmission range of the second gas detector.

The first and second gas detectors may communicate in a self-forming network that forms as the first and second gas detectors are carried within transmission range of each other. The second gas detector may be a master device that is paired with the first gas detector and with additional gas detectors that each have environmental condition detection circuitry, data processing circuitry, and wireless communication circuitry as described above, and are capable of providing an alert notification to users carrying the additional gas detectors.

In various embodiments, when communicating the alert to the second gas detector, the data processing circuitry of the first gas detector may include an indicator of a number of hops or levels of transmission of the alert with the communication, and before transmitting the alert to another gas detector or device, the data processing circuitry of the second gas detector increments the indicator and includes the incremented indicator with the transmission to the another gas detector or device.

In various embodiments, the alert system may further include additional gas detectors or devices that receive the alert from the first gas detector or the second gas detector with an indicator of the number of hops or levels of transmission of the alert. Each of the additional gas detectors or devices increments the indicator received with the respective alert before transmitting the alert to yet another gas detector or device.

In various embodiments, in response to receipt of an alert, the data processing circuitry of the second gas detector and/or the additional gas detectors or devices may determine whether to provide an alert notification to a user and/or transmit the alert to yet another gas detector or device based on at least one of a determined proximity to a gas detector or device that transmitted the alert, a determined duration of time from when a gas detector or device transmitted the alert, a determined severity of the hazardous environmental condition indicated by the received alert, or the indicator of the number of hops or levels of transmission of the received alert.

Also described herein is a method of communicating an alert in a network of gas detectors in wireless transmission range of one another. Each gas detector is configured to be carried by a user and includes environmental condition detection circuitry, data processing circuitry, and wireless communication circuitry. In various embodiments, the method includes, for each gas detector, detecting an environmental condition in a vicinity of the respective gas detector, wherein the environmental condition includes a temperature in the vicinity of the gas detector; communicating detection data based on the detected temperature to the data processing circuitry of the respective gas detector; in response to detection of a hazardous temperature condition by a first gas detector, providing an alert notification to the user carrying the first gas detector and communicating the alert to one or more second gas detectors via the wireless communication circuitry of the first gas detector; and in response to receipt of an alert from the first gas detector, transmitting the alert to yet another gas detector or device via the wireless communication circuitry of the respective second gas detector.

The method may further comprise including an indicator of a number of hops or levels of transmission of the alert when communicating the alert to the one or more second gas detectors, and before transmitting the alert from the one or more second gas detectors to yet another gas detector or device, further incrementing the indicator of the number of hops or levels of transmission and including the further incremented indicator with the transmission.

The method may further comprise determining a sensory output of the alert notification based on at least one of a determined proximity to the gas detector or device that transmitted the alert, a determined duration of time from when a gas detector or device transmitted the alert, a determined severity of the hazardous temperature condition indicated by the received alert, or the indicator of the number of hops or levels of transmission of the received alert.

DETAILED DESCRIPTION

Figure 1:
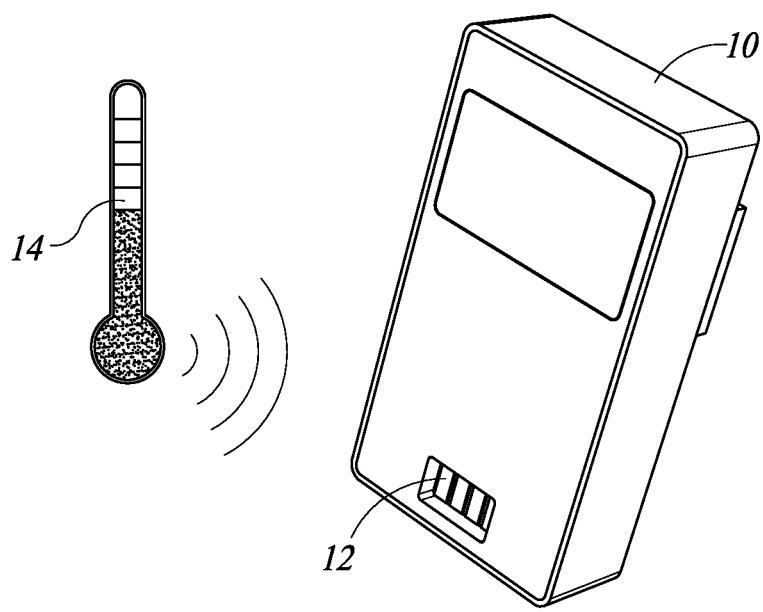
FIG. 1 is a pictorial diagram illustrating a gas detector that measures ambient temperature using a temperature sensor.
Figure 2:
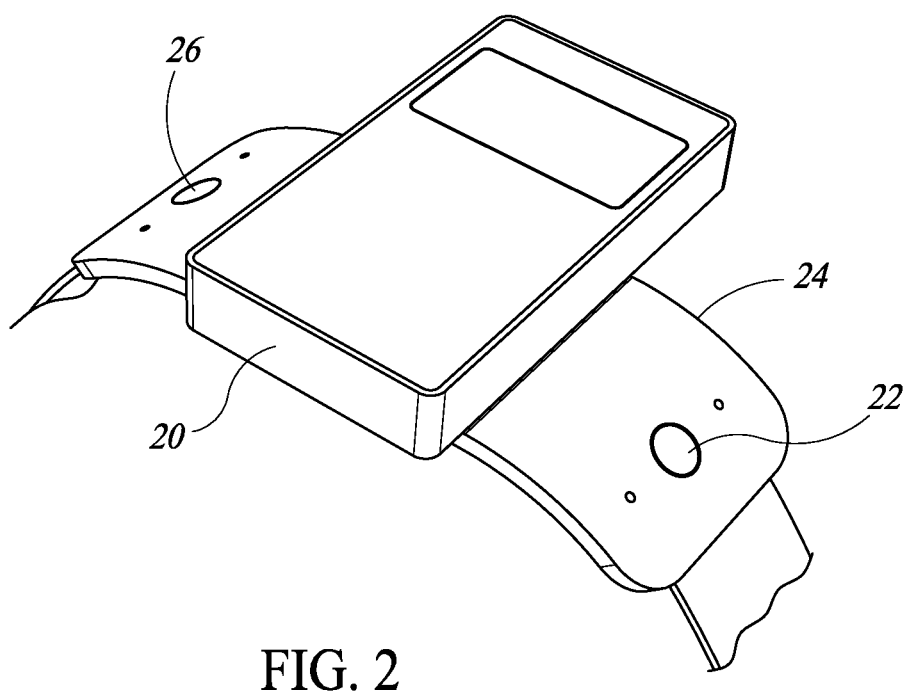
FIG. 2 illustrates a gas detector in an alternate configuration that measures biometric and/or ambient temperature using sensors.

FIG. 1 illustrates one example of a gas detector 10 that has a temperature sensor interfaced to the gas detector. In various embodiments, a temperature sensor 12 may be built into the gas detector 10 or into a substrate holding or enclosing the gas detector. Alternatively, a temperature sensor 14 may be an external temperature sensor that is connected to the gas detector 10 through a wired or wireless communication connection. In various embodiments, the temperature sensor 12, 14 is configured to measure ambient temperature of the environment around the gas detector 10. Alternatively, or in addition, the gas detector 10 may incorporate a biometric sensor that measures body temperature of the user wearing or holding the gas detector 10. For example, FIG. 2 illustrates a gas detector 20 (which may be similar to or the same as the gas detector 10) coupled to a substrate 24 that in turn can be strapped to or carried by a user. A temperature sensor 22 is built into the substrate 24. In various embodiments, more than one temperature sensor 12, 14, 22 may be interfaced to the gas detector 10, 20 measuring both ambient temperature and body temperature.

In operation, when the temperature sensor 12, 14, 22 detects a temperature (ambient or biometric) that meets or exceeds a high (hot) or low (cold) threshold or limit, the gas detector 10, 20 will initiate an alert to notify the user of the alert condition. Various forms of alert notification may be provided, including (but not limited to) a loud audible alarm, visible indicators in the form of flashing lights (typically LEDs), and/or vibration of the gas detector 10, 20.

Alert notification provided by the gas detector 10, 20 may be triggered upon detection of various conditions by the temperature sensor 12, 14, 22, including but not limited to:

1. If the measured temperature is beyond user-configurable upper and/or lower limits, or
 2. If the measured temperature is sustained for a period of time beyond user-configurable upper and/or lower limits, or
 3. A combination of the above.

The upper and lower limits for ambient temperature and/or biometric (body) temperature may be independent or shared. For example, different numeric thresholds may independently be established for measurements of ambient temperature and/or biometric temperature, and if a threshold or limit for either type of temperature measurement is met or exceeded, an alert with a corresponding notification to the user may be generated. In another example, a numeric threshold or limit for an ambient temperature alert may depend on a measured biometric temperature of the user carrying the gas detector, or vice versa. Likewise, numeric thresholds for initiating either an ambient temperature alert or biometric temperature alert may depend on other criteria including, for example, the time period over which temperatures exceeding a threshold or limit have been detected. By combining temperature measurements and time duration of a measured excessive temperature, the determination of alert conditions may be more robust. The threshold limits for either or both ambient and biometric temperature alerts may be preset and/or user configurable.

Moreover, based on the source of the temperature alert, i.e., ambient or biometric, different treatment of the alert conditions may be implemented. For example, excessive biometric temperature may be considered a higher risk for the individual carrying the gas detector and thus the alert notification of the excessive temperature may be more prominent (louder, brighter, stronger, etc.). In embodiments where time duration of an excessive temperature is also measured, the type and form of alert notification may become more prominent as the duration of the excessive temperature measurements increases.

One or more additional sensors may also be implemented in the gas detector 10, 20 along with a temperature sensor. For example, a humidity sensor 26 may detect humidity of the environment in the vicinity of the gas detector 20. Humidity measurements with user-defined or preset humidity threshold limits may be included in the alert determination. For example, an alert condition may be determined more quickly (i.e., over a shorter duration of time) if an excessive temperature is measured in the presence of high humidity. Conversely, an excessive temperature measurement over the same period of time may present a lower risk to the user in the presence of lower humidity, and thus an alert condition may be determined after a longer period of time has elapsed.

In some embodiments, additional thresholds may be established and met, and alert conditions determined, regardless of time duration or other environmental conditions, including humidity. For example, if a sufficiently high or low temperature is detected, the gas detector may immediately initiate an alert with a corresponding notification to the user.

Users of the gas detectors 10, 20 may be individuals that work in a confined space or other hazardous work environment, such as in a refinery, power plant, chemical plant, or mine. The gas detectors 10, 20 are configured to detect harmful conditions including excessive temperature levels while the individuals carrying the gas detectors are working in the hazardous work environment. The gas detectors 10, 20 are also configured to detect the presence or lack of certain gases. The users may each wear or otherwise carry a gas detector for monitoring the users' exposure to hazardous conditions.

Figure 3:
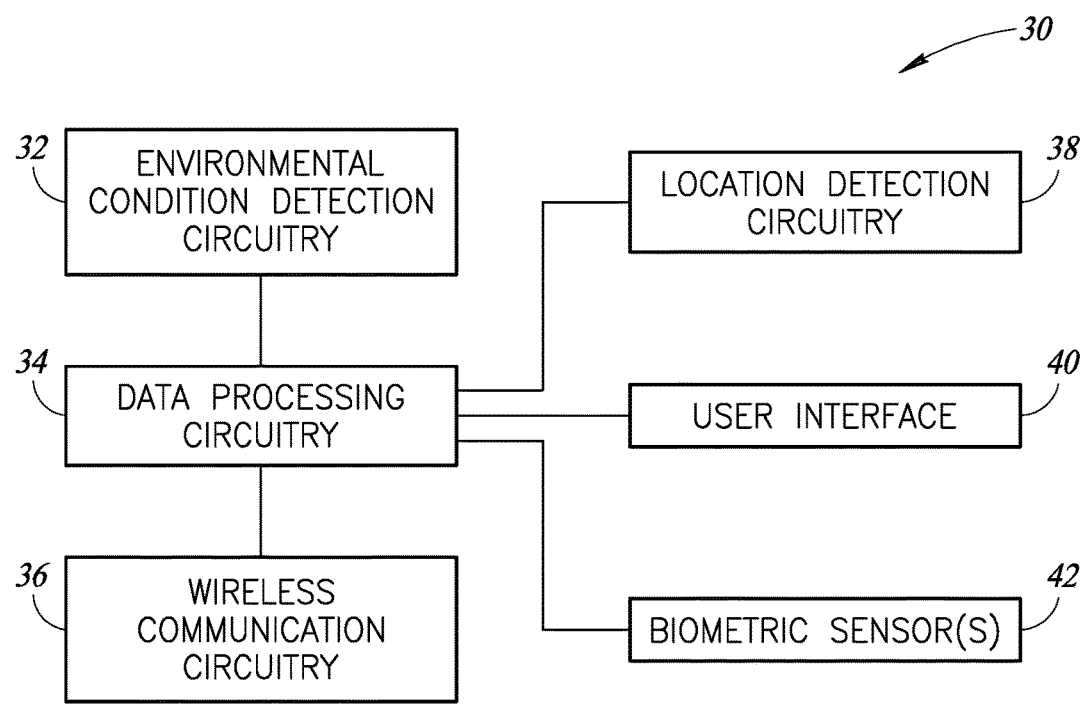
FIG. 3 is a block diagram of an embodiment of a gas detector.

As illustrated in FIG. 3, a gas detector 30 (such as the gas detectors 10, 20 or other gas detectors described herein) generally comprises environmental condition detection circuitry 32, including one or more sensors adapted to detect environmental conditions in the vicinity of the gas detector 30. The environmental condition detection circuitry 32 is configured produce detection data based on measurements obtained by the one or more sensors. The gas detector 30 further comprise data processing circuitry 34 and wireless communication circuitry 36. The data processing circuitry 34 may include one or more processors that operate in accordance with logic in the gas detector 30, e.g., program instructions that are stored in a memory. Other embodiments of the data processing circuitry 34 may include application-specific integrated circuits or other computing hardware and/or software configured to implement the operations of a gas detector as described herein.

The wireless communications circuitry 36 in a gas detector may include a transceiver that is adapted to receive and transmit signals, such as electromagnetic or sound-based signals, that carry information to or from the gas detector and other gas detectors. The wireless communications circuitry 36 thus provides an interface for communication with other gas detectors or devices (such as a programmed mobile phone) in the alert system. In some embodiments, the gas detector 30 may further include location detection circuitry 38 adapted to determine a relative or absolute physical location of the respective gas detector, including but not limited to GPS, cellular or wireless network triangulation circuitry. Location data produced by the locating circuitry 38 may be communicated to one or more other gas detectors or devices via the wireless communications circuitry 36 in addition to, or alternative to, communication of detection data derived from the measurements obtained by the one or more sensors in the detection circuitry 32.

The interface provided by the wireless communications circuitry 36 may transmit data indicating the temperature of the surrounding environment and/or the amount of hazardous gas that a user of the gas detector 30 has been exposed to, and possibly the location of the user, to one or more other gas detectors 30. In the system shown in FIG. 4, a master gas detector 52 (or an alternative computing device) is paired with multiple slave gas detectors 54, 56, 58. The master gas detector 52 includes logic that causes the gas detector 52 to log data received from the gas detectors 54, 56, 58, to monitor communications for alert conditions, and to relay alert information to other gas detectors 54, 56, 58 via the wireless medium 60.

Temperature, gas exposure, and possibly location data of a gas detector 54, 56, 58 may be transmitted to the gas detector 52 on a periodic basis. The time between transmissions of each gas detector 54, 56, 58 may be configured automatically and/or manually. For example, if it is anticipated that the user will be entering an area with higher possibility of exposure to high or low temperatures or exposure to hazardous gases, the user may carry a gas detector 54, 56, 58 that is configured to transmit temperature and/or gas exposure information to the gas detector 52 more frequently. If a measured temperature or gas exposure detected by the gas detector 54, 56, 58 approaches a dangerous level, the gas detector 54, 56, 58 may automatically commence to transmit the temperature or gas exposure information to gas detector 52 more frequently. There may be, for example, one or more temperature or gas exposure thresholds or limits programmed within the gas detector 54, 56, 58 that, when met, may cause the gas detector to increase the frequency of transmission of temperature or gas exposure information to the master gas detector 52. In some embodiments, the gas detector 54, 56, 58 may monitor temperature and/or gas exposure without transmitting information to the master gas detector 52 or other gas detectors until an alert is generated by the detector 14, 16, 18 detecting a temperature or gas exposure that meets a programmed threshold. In yet other embodiments, a gas detector 14, 16, 18 may not transmit temperature or gas exposure information to other gas detectors, but only transmit alert information to other gas detectors when the detector 14, 16, 18 generates a local alert.

Figure 6:
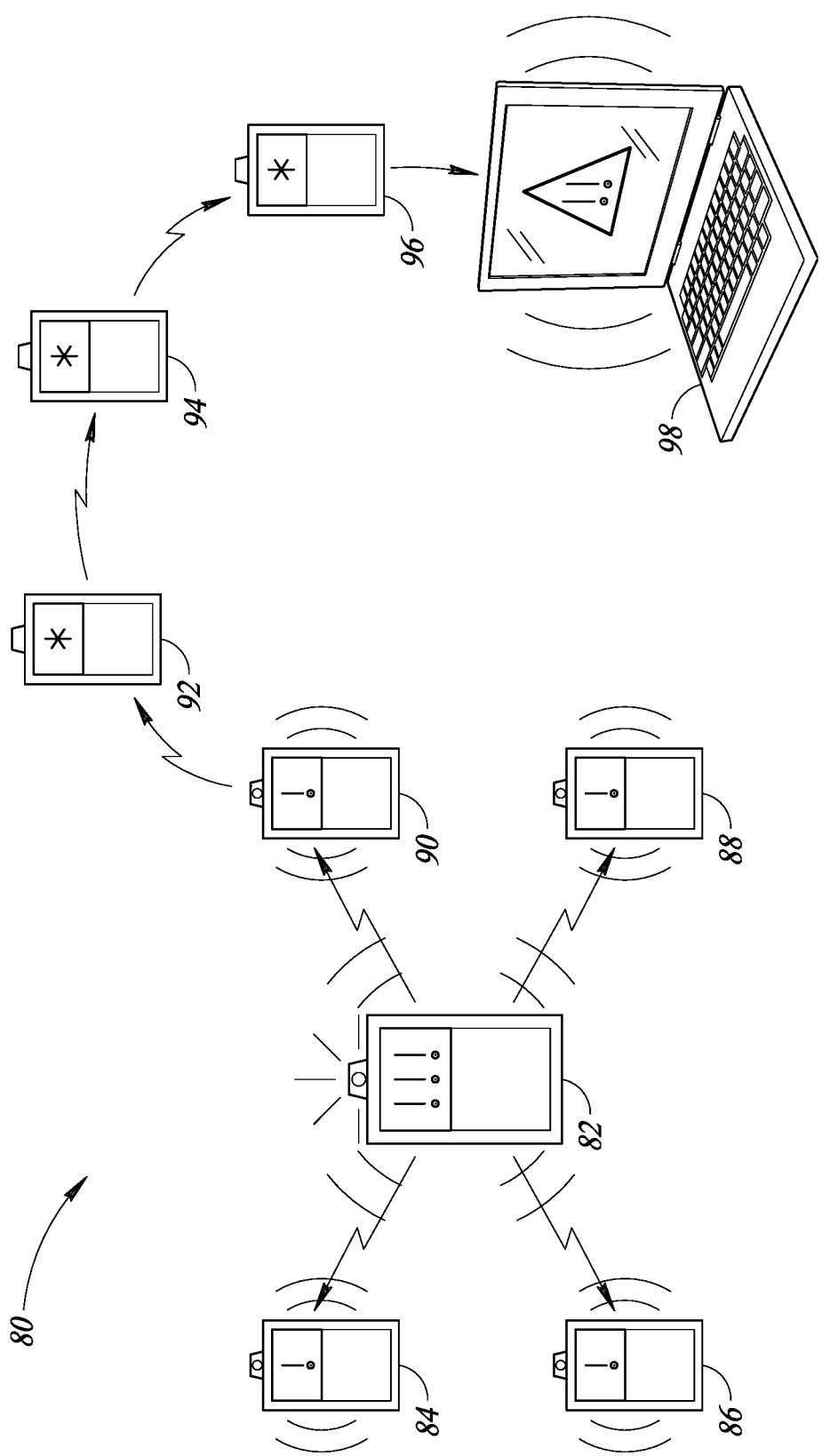
FIG. 6 is a pictorial diagram illustrating an example of an alert relay/propagation between gas detectors and other compatible devices up to a control room/supervisor.

As described above, a gas detector 10, 20, 54, 58, 58 may further transmit information concerning an alert to a peer gas detector, a master gas detector 52, or a central station 98 (see FIG. 6). Wireless communication between gas detectors may be in the form of a sound or electromagnetic signal.

Figure 4:
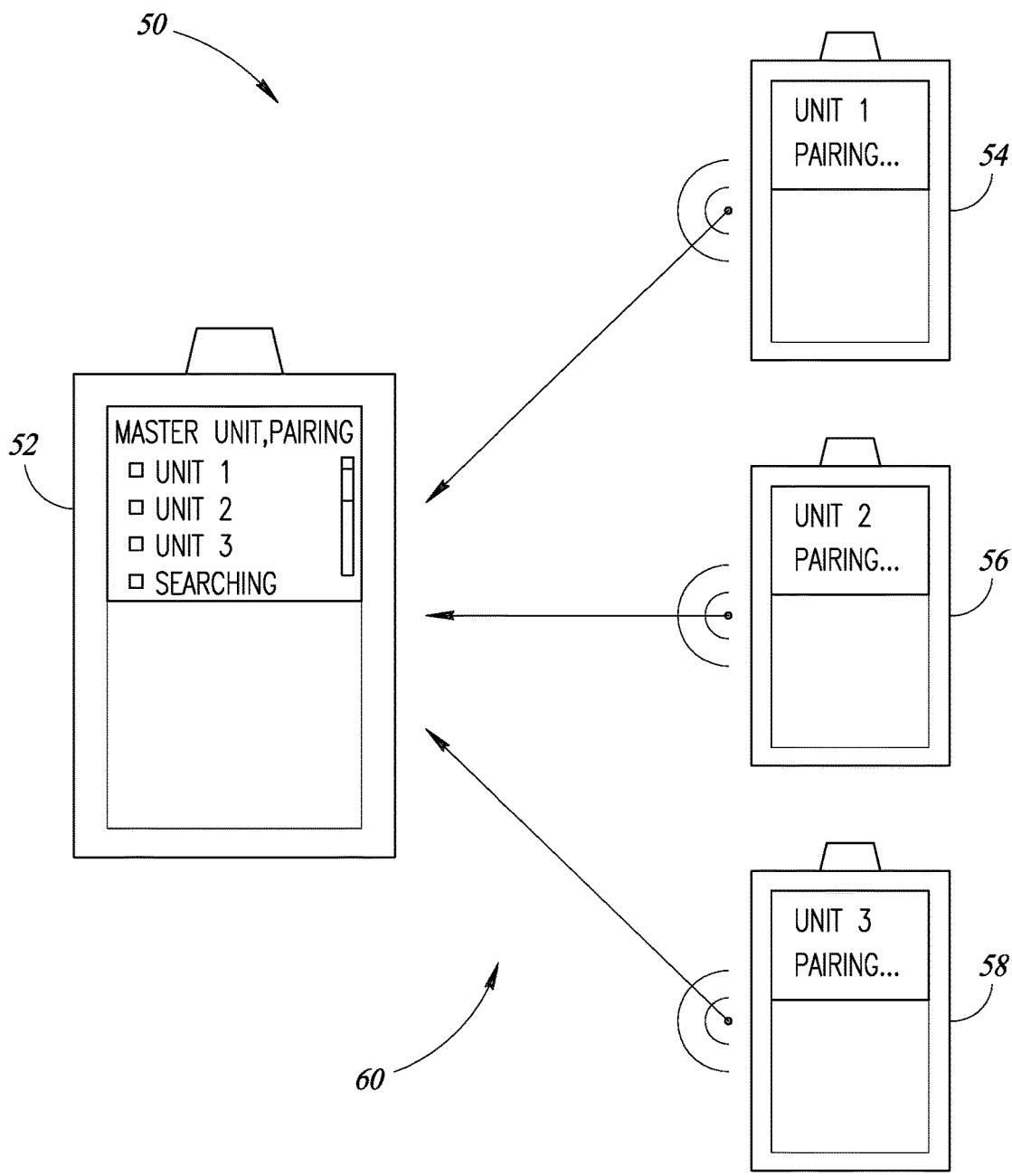
FIG. 4 is a pictorial diagram illustrating an alert system with multiple detectors that are usable for monitoring one or more environmental conditions.

Detector-to-detector alert systems provide a way to disseminate determined alerts to other gas detectors or devices when one or more gas detectors detect an unsafe temperature and/or other unsafe environmental condition. As will be apparent from the following description, alert information can be disseminated among gas detectors in the system in different ways. In some embodiments, information concerning an alert may be transmitted as a wireless broadcast from a first gas detector to other gas detectors within the first detector's range of transmission. This broadcast may occur ad hoc or the information may be transmitted through a pre-established or self-forming mesh or star network of gas detectors and other compatible devices, such as network repeaters, base stations, hubs, etc. In other embodiments, information concerning an alert may be transmitted as a wireless communication to a master device (e.g., as illustrated in FIG. 4), which may be another gas detector or a different non-detector computing device that facilitates further communication of the alert information to peer gas detectors in the system.

As contemplated herein, self-forming networks may include other gas detectors and non-detector devices that are compatible with the detector-to-detector alert system. The wireless medium used to convey alert information between gas detectors and other devices may include (but are not limited to) electromagnetic communication, e.g., radio frequency or light-based wireless systems, as well as inaudible high-frequency sound-based communication or audible sound-based communication, or any combination of the above. For example, lower power electromagnetic communication systems may operate according to ZigBee, Wi-Fi, or Bluetooth standards. Alternatively or in addition, infrared or other light-based signals may be used. Audible or inaudible sounds may be transmitted and received between gas detectors. Cellular and/or satellite communication technology may be used in yet other applications or situations.

While embodiments of the alert systems and methods described herein relate to use of gas detectors with temperature sensors and monitoring of temperature in the vicinity of the gas detectors (including biometric sensing of the user's body temperature), the alert systems may also be used to monitor the exposure of individuals to other hazardous conditions or materials. The detector-to-detector alert systems and methods described herein may be embodied in different forms as required for monitoring temperature and possibly other environmental conditions, and notifying individuals when conditions indicate a hazardous environment.

The alert systems and methods described herein provide for sharing of alert information among individuals carrying gas detectors in a work area, which may be a confined space or other work area. Each individual entering the area may be provided with a gas detector, such as a gas detector 10, 20, that monitors temperature in the vicinity of the gas detector. When the temperature sensor(s) in a gas detector detects a temperature such that an alert threshold is met, the gas detector initiates an alert notification to the individual carrying the gas detector as well as communicates with other gas detectors carried by individuals in the transmission range of the gas detector. The gas detector may also initiate communication with emergency responders and/or a central station.

In some embodiments, the gas detector may include additional sensors that monitor biometric information, such as heart rate, blood pressure, or other health indicators of the individual carrying the gas detector. The gas detector may include a panic button (e.g., in a user interface 40 as shown in FIG. 3) that, when activated by an individual, initiates an alert that may be communicated to other gas detectors in the system.

Notably, the peer-to-peer communication implemented by the gas detectors in the alert system disclosed herein allows temperature alert information and other alert information to be quickly propagated among gas detectors in the vicinity of the gas detector that is generating the alert, without requiring that the alert information be first communicated to a centralized remote server. The improved detector-to-detector communication allows other individuals who may be exposed to the hazardous condition to more quickly evaluate the situation and possibly evacuate from the hazardous area.

As described earlier, FIG. 4 illustrates an embodiment of an alert system with multiple gas detectors that are usable for monitoring environmental conditions including temperature (ambient and/or biometric). The system includes a master gas detector 52 or an alternative computing device such as a mobile phone (e.g., programmed with an app) that is paired to one or more slave gas detectors 54, 56, 58 for logging, monitoring, and relaying alerts via a wireless medium 60. As will be seen herein, variations in the arrangement, type, and operation of the components shown in the figures may be made without departing from the scope of the present disclosure. Additional, different, or fewer components or different communication topologies may be employed.

Returning to FIG. 3, when generating a local alert, a gas detector 30 may produce an alert notification to the individual user carrying the gas detector 30. The alert notification may include any form of visual, aural, or haptic sensory output to the individual. For example, one or more LEDs on the gas detector 30 may produce a flashing signal, while an alarm may sound and/or the gas detector may vibrate. The gas detector 30 may include a user interface 40, such as a button, that allows the individual carrying the gas detector 30 to acknowledge the local alert. If the individual does not acknowledge the local alert, the gas detector 30 may heighten the severity of the alert that is transmitted to other gas detectors, as described herein.

While FIG. 4 illustrates an embodiment in which gas detectors 52, 54, 56, 58 are arranged in a master-slave relationship where the master detector or device 52 facilitates the dissemination of alerts between peer gas detectors 54, 56, 58, other embodiments of the alerting system may include direct ad hoc communications between peer gas detectors. In yet other embodiments, the gas detectors 52, 54, 46, 58 may be organized in one or more self-forming or prescribed networks where gas detectors are aware of peer gas detectors that are adjacent in the network and communicate alert information directly with such adjacent gas detectors.

Figure 5:
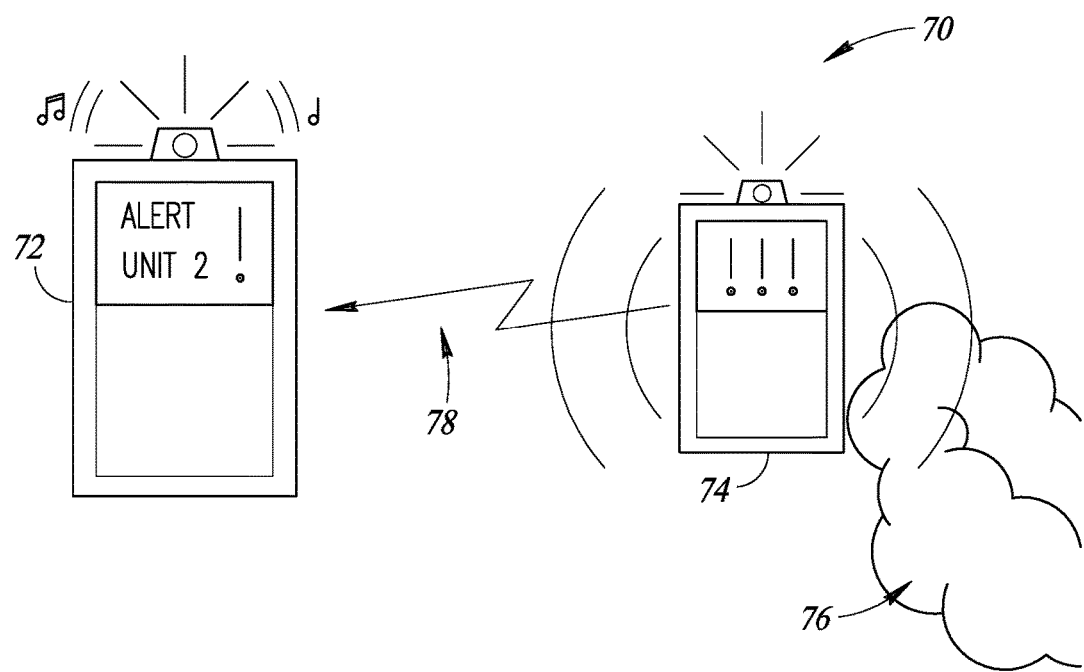
FIG. 5 is a pictorial diagram illustrating an alert system with alert propagation between gas detectors via a wireless medium.

FIG. 5 illustrates an alert system 70 providing an alert propagation between gas detectors 72 and 74 via a wireless medium 78. For example, when the gas detector 74 has detected a local environmental condition 76 (e.g., excessive high or low temperature or hazardous gas) that the merits generating an alert, a local alert notification is provided to the user of the gas detector 74 and information concerning the alert is transmitted via the wireless communications circuitry in the gas detector 74 to the wireless communications circuitry in the peer gas detector 72. As noted earlier, the wireless medium 78 may provide for electromagnetic or sound-based communication of information between the gas detector 72 and the gas detector 74.

In some embodiments, for example, the gas detectors 72, 74 may be tuned to a particular frequency or channel to communicate information with peer gas detectors. Encryption technologies may be used to secure the communications between gas detectors 72, 74. When a gas detector 72, 74 is not transmitting information, the wireless communications circuitry in the detector may periodically or continuously listen for communications from other gas detectors 72, 74 at the particular frequency or channel. A gas detector 72, 74 that has detected a hazardous condition and is generating a local alert may thus transmit information concerning the alert to other gas detectors 72, 74 that are listening to the particular frequency or channel. In such embodiments, the alert may be broadcast to other gas detectors 72, 74 within the vicinity or transmission range of the alert-generating detector.

In cases where multiple gas detectors 72, 74 may attempt to simultaneously broadcast alert information to other gas detectors, contention protocols may be used to ensure that each information broadcast is properly received by the other detectors. For example, overlapping information broadcasts may be repeated by the gas detectors 72, 74 at intervals that separate the contending transmissions. Different signal encoding technologies may also be used to help separate potentially contending transmissions.

In alert systems where the gas detectors 72, 74 are organized in a network, whether the network be preset or self-forming, the gas detectors 72, 74 may address their transmissions of alert information to known adjacent gas detectors. If desired, handshake technologies or acknowledgements may be used to ensure that communicated alert information has been properly received by the adjacent gas detectors.

The alert vicinity of a gas detector 72, 74 may be ad hoc, for example as gas detectors move in and out of transmission range of one another. In such embodiments, those gas detectors 72, 74 that are within the range of transmission of the alert-generating detector may receive a broadcast of the alert information from the alert-generating detector. In other embodiments, the alert vicinity of a gas detector 72, 74 may be user defined (e.g., by manually pairing gas detectors and other devices, or otherwise organizing the communication paths between the gas detectors and devices). Gas detectors 72, 74 may be configured to periodically transmit a polling signal to other gas detectors 72, 74 within the transmission range of the gas detector and receive information from the other gas detectors identifying their presence. The gas detectors 72, 74 may also exchange information to determine adjacency of the gas detectors in a network topology.

Gas detectors 72, 74 receiving alert information may in turn transmit some or all of the alert information to yet other gas detectors or devices (such as a programmed mobile phone) in their alert vicinity. Alert information may thus be propagated from one gas detector 72, 74 to another gas detector 72, 74 until all gas detectors or other devices in the system have been alerted. Alternatively, the transmission of alert information may be controlled so that only a subset of gas detectors and devices in the system receive and/or act on the alert information. Controlling the transmission of alert information may be advisable, for example, in large industrial plants where a local alert may be pertinent to individuals within a certain proximity to the alert-generating gas detector, but not to all individuals in the entire industrial plant.

When alert information is transmitted, the alert information may include a count of the number of hops or levels of transmission of the alert information. When the number of hops or levels of transmission reaches a threshold, further retransmission of the alert information may be stopped. The number of hops or levels of transmission may be programmed in the gas detectors or it may be dynamically determined according to one or more criteria that, for example, considers the severity of the alert or other reasons for expanding or reducing the reach of transmission of alert information.

The sensory output of an alert notification may be distinct depending whether the alert is locally generated or is received from another gas detector. Distinct notifications help distinguish between a local alert that may represent a higher risk to the individual carrying the gas detector, and a propagated alert that may represent a lower risk to the individuals carrying the other gas detectors. For example, different combinations of light, sound, or vibrations may signal whether the alert has been locally generated or received from another gas detector.

FIG. 6 illustrates an example in which an alert is relayed or propagated between gas detectors and/or other compatible devices 82-96 up to a control room/supervisor 98. A distinct alert is given at the source that is typical of a gas detector, and alerts given at other levels of propagation are distinguishable from the alert at the source detector. More specifically, at the source (i.e., the alert-generating gas detector 82), a distinct alert notification is made indicating a "Level 0" alert. Such alert notification may be typical of known gas detectors. As alert information is transmitted by the alert-generating gas detector 82 to other peer gas detectors 84, 86, 88, 90 in the system, and from a peer detector to yet other detectors or devices 92, 94, 96, the alert notifications may progress at each level of transmission from a "Level 0" alert to a "Level 1," "Level 2," "Level 3," etc., alert depending on the number of times the alert information has been transmitted. At each level, the alert notification made by the respective gas detectors 84-96 may be clearly distinguishable from the Level 0 alert notification made by the alert-generating detector 82. Generally, it may be expected that at each incrementally higher level of transmission, the respective gas detector in the transmission path (e.g., gas detectors 92-96) is farther away from the original alert-generating detector 82 and thus the form of notification of the alert by the respective gas detector may be commensurate with the lower expected risk presented to the user of the gas detector. In such cases, for example, higher risk notifications may include multiple elements of sensory output, such as light, sound, or vibration, while lower risk notifications may be limited, e.g., to one such mode of communication. In other cases, the color or frequency of light, sound, or vibration may be different according to different levels of transmission or determined risk presented by a particular alert.

Alert information may also include time data representing a time or passage of time from when the alert was initially generated. The type and form of alert notifications at each level of transmission of the alert information may be modified in accordance with the time or passage of time data in the alert information.

At each level, the gas detectors 82-96 may include logic operable by the data processing circuitry in the respective gas detectors to determine whether propagated alerts should be retransmitted to yet other gas detectors or devices. In some cases, the gas detectors 84-96 receiving alert information may not provide any notification of the alert but simply act as a pass-through device for transmitting the alert information to a final destination, e.g., a central alert monitoring board 98 used by an operator of the industrial plant. In other cases, logic operable by the data processing circuitry in the respective gas detectors 84-96 (as well as the originating detector 82) may determine on a case-by-case basis whether to evaluate the received alert information and/or act on the alert information.

Embodiments of the gas detector 30 (see FIG. 2), which may represent any of the gas detectors described herein, may include a user interface 40, e.g., a button, that allows the local user of the gas detector to turn off some or all alert propagation to other detectors or devices. For example, a user may wish to use the gas detector 30 to identify a small gas leak in an industrial process. In such case, the amount of gas and/or the temperature around the gas detector 30 may not present a risk to the user. The user may manually place the gas detector 30 in locations where a leak is suspected. Should the gas detector 30 detect the presence of a gas leak or excessive temperature in the particular location, a local alert may be provided to the user of the detector 30 without alerting other gas detectors in the detector's vicinity or transmission range. In some embodiments, it may be preferable to limit the time in which the alert propagation is turned off so that the gas detector 30 may automatically return to normal operation after a period of time. Alternatively, the gas detector 30 may allow the user to turn off the alert propagation only while the user continuously activates the user interface 40, e.g., by holding down the button.

The alert information propagated in the alert system, such as the alert system 80 in FIG. 6, may include some or all information that is produced by or otherwise stored in the alert-generating gas detector 82. For example, in addition to reporting an excessive temperature and/or the presence or lack of a particular gas, the alert information may include data indicating the magnitude of the temperature and/or the amount of gas detected. Additional data such as location data of the gas detector 82 and unique identification of the individual carrying the gas detector 82 may be included. Alternatively, or in addition, work order data or device information specific to the gas detector 82 may be communicated. Accordingly, when alert information is propagated to other detectors 84-96 within the alert system 80, appropriate responses to the alert information may be determined and acted upon by other gas detectors 84-96 in the system.

Thus, in various embodiments, an alert system as described above may include a first gas detector and a second gas detector. The first gas detector includes environmental condition detection circuitry, data processing circuitry, and wireless communication circuitry, and is configured to be carried by a first user. The environmental condition detection circuitry of the first gas detector detects environmental conditions in a vicinity of the first gas detector and communicates detection data to the data processing circuitry of the first gas detector.

The second gas detector also includes environmental condition detection circuitry, data processing circuitry, and wireless communication circuitry, and is configured to be carried by a second user. The environmental condition detection circuitry of the second gas detector detects environmental conditions in a vicinity of the second gas detector and communicates detection data to the data processing circuitry of the second gas detector.

In response to detection of a hazardous environmental condition by the first gas detector, the data processing circuitry of the first gas detector provides an alert notification to the first user and communicates the alert to the second gas detector via the wireless communication circuitry of the first gas detector. In response to receipt of an alert from the first gas detector, the data processing circuitry of the second gas detector transmits the alert to another gas detector or device via the wireless communication circuitry of the second gas detector.

In various embodiments, in response to detection of a hazardous environmental condition by the second gas detector, the data processing circuitry of the second gas detector provides an alert notification to the second user and communicates the alert to the first gas detector via the wireless communication circuitry of the second gas detector, and in response to receipt of an alert from the second gas detector, the data processing circuitry of the first gas detector transmits the alert to another gas detector or device via the wireless communication circuitry of the first gas detector.

The first gas detector may broadcast the alert in an ad hoc communication to the second gas detector without knowing that the second gas detector is in transmission range of the first gas detector. Likewise, the second gas detector may broadcast the alert in an ad hoc communication to the first gas detector without knowing that the first gas detector is in transmission range of the second gas detector.

The first and second gas detectors may communicate in a self-forming network that forms as the first and second gas detectors are carried within transmission range of each other. The second gas detector may be a master device that is paired with the first gas detector and with additional gas detectors that each have environmental condition detection circuitry, data processing circuitry, and wireless communication circuitry and are capable of providing an alert notification to users carrying the additional gas detectors.

In various embodiments, the alert system may further include a third gas detector that also has environmental condition detection circuitry, data processing circuitry, and wireless communication circuitry, and is configured to be carried by a third user. The environmental condition detection circuitry of the third gas detector detects environmental conditions in a vicinity of the third gas detector and communicates detection data to the data processing circuitry of the third gas detector.

In response to detection of a hazardous environmental condition by the first gas detector, the data processing circuitry of the first gas detector further communicates the alert to the third gas detector via the wireless communication circuitry of the first gas detector, and in response to receipt of an alert from the first gas detector, the data processing circuitry of the third gas detector transmits the alert to another gas detector or device via the wireless communication circuitry of the third gas detector.

The first gas detector may further include location detection circuitry, and in response to detection of a hazardous environmental condition by the first gas detector, the data processing circuitry of the first gas detector further communicates location data reflecting a location of the first gas detector to the second gas detector via the wireless communication circuitry of the first gas detector.

The first gas detector may further include one or more biometric sensors configured to monitor biometric information of the first user, and in response to detection of a hazardous environmental condition by the first gas detector, the data processing circuitry of the first gas detector further communicates the biometric information of the first user to the second gas detector via the wireless communication circuitry of the first gas detector.

In various embodiments, when communicating the alert to the second gas detector, the data processing circuitry of the first gas detector includes an indicator of a number of hops or levels of transmission of the alert with the communication, and before transmitting the alert to another gas detector or device, the data processing circuitry of the second gas detector increments the indicator of the number of hops or levels of transmission of the alert and includes the incremented indicator with the transmission to the another gas detector or device. The another gas detector or device may be a third gas detector that includes environmental condition detection circuitry, data processing circuitry, and wireless communication circuitry, and is configured to be carried by a third user. The environmental condition detection circuitry of the third gas detector detects environmental conditions in a vicinity of the third gas detector and communicates detection data to the data processing circuitry of the third gas detector. In response to receipt of the alert and incremented indicator from the second gas detector, the data processing circuitry of the third gas detector further increments the indicator and transmits the alert with the further incremented indicator to yet another device via the wireless communication circuitry of the third gas detector.

In various embodiments, the alert system may further include additional gas detectors or devices that receive the alert from the first gas detector or the second gas detector with an indicator of the number of hops or levels of transmission of the alert. Each of the additional gas detectors or devices increments the indicator received with the respective alert before transmitting the alert to yet another device. Each additional gas detector is configured to be carried by a user and includes environmental condition detection circuitry, data processing circuitry, and wireless communication circuitry. The environmental condition detection circuitry of each additional gas detector detects environmental conditions in a vicinity of the additional gas detector and communicates detection data to the data processing circuitry of the additional gas detector.

In various embodiments, in response to receipt of an alert, the data processing circuitry of the second gas detector and/or the additional gas detectors or devices determine whether to provide an alert notification to a user and/or transmit the alert to yet another gas detector or device based on at least one of a determined proximity to a gas detector or device that transmitted the alert, a determined duration of time from when a gas detector or device transmitted the alert, a determined severity of the hazardous environmental condition indicated by the received alert, or the indicator of the number of hops or levels of transmission of the received alert.

When it is determined to provide an alert notification to a user, a sensory output of the alert notification may be determined based on at least one of a determined proximity to the gas detector or device that transmitted the alert, a determined duration of time from when a gas detector or device transmitted the alert, a determined severity of the hazardous environmental condition indicated by the received alert, or the indicator of the number of hops or levels of transmission of the received alert.

In various embodiments, in response to receipt of an alert from the first gas detector, the data processing circuitry of the second gas detector determines whether to provide an alert notification to the second user in addition to transmitting the alert to another gas detector or device.

The first and second gas detectors may further include a user interface that, when activated by a user, causes the data processing circuitry of the respective first or second gas detector to not transmit the alert to another gas detector or device.

Also described herein is a method of communicating an alert in a network of gas detectors in wireless transmission range of one another. Each gas detector is configured to be carried by a user and includes environmental condition detection circuitry, data processing circuitry, and wireless communication circuitry. In various embodiments, the method includes detecting an environmental condition in a vicinity of the respective gas detector; communicating detection data to the data processing circuitry of the respective gas detector; in response to detection of a hazardous environmental condition by a first gas detector, providing an alert notification to the user carrying the first gas detector and communicating the alert to one or more second gas detectors via the wireless communication circuitry of the first gas detector; and in response to receipt of an alert from the first gas detector, transmitting the alert to yet another gas detector or device via the wireless communication circuitry of the respective second gas detector.

The method may further comprise including an indicator of a number of hops or levels of transmission of the alert when communicating the alert to the one or more second gas detectors, and before transmitting the alert from the one or more second gas detectors to yet another gas detector or device, further incrementing the indicator of the number of hops or levels of transmission and including the further incremented indicator with the transmission.

In response to receipt of an alert, it may be determined whether to provide an alert notification to a user and/or transmit the alert to another gas detector or device based on at least one of a determined proximity to a gas detector or device that transmitted the alert, a determined duration of time from when a gas detector or device transmitted the alert, a determined severity of the hazardous environmental condition indicated by the received alert, or the indicator of the number of hops or levels of transmission of the received alert.

When it is determined to indicate an alert to a user, a sensory output of the alert notification may be further determined based on at least one of a determined proximity to the gas detector or device that transmitted the alert, a determined duration of time from when a gas detector or device transmitted the alert, a determined severity of the hazardous environmental condition indicated by the received alert, or the indicator of the number of hops or levels of transmission of the received alert.

It should be appreciated that the various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A gas detector, comprising:
  environmental condition detection circuitry that includes one or more sensors that detect the presence or lack of presence of a particular gas in a vicinity of the gas detector;
  data processing circuitry; and
  wireless communication circuitry,
  wherein the gas detector is configured to be carried by a user, wherein the environmental condition detection circuitry further includes one or more temperature sensors that detect a temperature in the vicinity of the gas detector and communicates temperature detection data to the data processing circuitry, at least one of the one or more temperature sensors being a biometric sensor configured to detect a body temperature of the user carrying the gas detector and at least one of the one or more temperature sensors detecting an ambient temperature in the vicinity of the gas detector, wherein the data processing circuitry detects a hazardous temperature condition when at least one of a body temperature of the user carrying the gas detector or an ambient temperature in the vicinity of the gas detector is beyond an upper and/or lower temperature limit for a period of time beyond a time limit, wherein the environmental condition detection circuitry further includes one or more humidity sensors that detect a humidity in the vicinity of the gas detector, and wherein the time limit varies depending on a magnitude of the detected humidity, and wherein, in response to detection of a hazardous temperature condition, the data processing circuitry of the gas detector provides an alert notification to the user carrying the gas detector.

2. The gas detector of claim 1, wherein the time limit further varies depending on a magnitude of at least one of the detected body temperature of the user or the ambient temperature.

3. The gas detector of claim 1, wherein a sensory output of the alert notification provided to the user varies depending on an amount of time beyond the time limit in which the detected body temperature of the user or the ambient temperature is beyond the upper and/or lower temperature limit.

4. The gas detector of claim 3, wherein the type and form of the alert notification becomes more prominent as the amount of time increases in which the detected body temperature or ambient temperature is beyond the upper and/or lower temperature limit.

5. An alert system, comprising:
a first gas detector according to claim 1, wherein the first gas detector is configured to be carried by a first user; and
a second gas detector according to claim 1, wherein the second gas detector is configured to be carried by a second user,
wherein, in response to detection of a hazardous temperature condition by the first gas detector, the data processing circuitry of the first gas detector provides an alert notification to the first user and communicates an alert to the second gas detector via the wireless communication circuitry of the first gas detector, and
wherein, in response to receipt of the alert from the first gas detector by the second gas detector, the data processing circuitry of the second gas detector transmits the alert to another gas detector or device via the wireless communication circuitry of the second gas detector.

6. The alert system of claim 5, wherein, in response to detection of a hazardous temperature condition by the second gas detector, the data processing circuitry of the second gas detector provides an alert notification to the second user and communicates an alert to the first gas detector via the wireless communication circuitry of the second gas detector, and
wherein, in response to receipt of the alert from the second gas detector by the first gas detector, the data processing circuitry of the first gas detector transmits the alert to another gas detector or device via the wireless communication circuitry of the first gas detector.

7. The alert system of claim 5, wherein the first gas detector broadcasts the alert in an ad hoc communication to the second gas detector without knowing that the second gas detector is in transmission range of the first gas detector.

8. The alert system of claim 5, wherein the first and second gas detectors communicate in a self-forming network that forms as the first and second gas detectors are carried within transmission range of each other.

9. The alert system of claim 5, wherein the second gas detector is a master device that is paired with the first gas detector and with additional gas detectors as slave devices, wherein each of the additional gas detectors has environmental condition detection circuitry, data processing circuitry, and wireless communication circuitry according to claim 1, and is capable of providing an alert notification to respective users carrying the additional gas detectors.

10. The alert system of claim 5, wherein when communicating the alert to the second gas detector, the data processing circuitry of the first gas detector includes an indicator of a number of hops or levels of transmission of the alert with the communication, and
wherein, before transmitting the alert to another gas detector or device, the data processing circuitry of the second gas detector increments the indicator of the number of hops or levels of transmission of the alert and includes the incremented indicator with the transmission to the another gas detector or device.

11. The alert system of claim 10, further comprising additional gas detectors or devices that receive the alert from the first gas detector or the second gas detector with the indicator of the number of hops or levels of transmission of the alert, wherein each of the additional gas detectors or devices increments the indicator received with the respective alert before transmitting the alert to yet another gas detector or device.

12. The alert system of claim 11, wherein, in response to receipt of an alert, the data processing circuitry of the second gas detector and/or the additional gas detectors or devices determines whether to provide an alert notification to a user and/or transmit the alert to yet another gas detector or device based on at least one of a determined proximity to the gas detector or device from which the alert was received, a determined duration of time from when the alert was transmitted, a determined severity of the hazardous environmental condition indicated by the alert, or the indicator of the number of hops or levels of transmission of the alert.

13. The alert system of claim 12, wherein, in response to receipt of the alert, the data processing circuitry of the additional gas detectors or devices determines whether to provide the alert notification to the user and/or transmit the alert to yet another gas detector or device based on the indicator of the number of hops or levels of transmission of the alert.

14. The alert system of claim 5, wherein when communicating the alert from the first gas detector to the second gas detector, the data processing circuitry of the first gas detector includes an indicator of a number of hops or levels of transmission of the alert with the communication,
wherein, before transmitting the alert from the second gas detector to another gas detector or device, the data processing circuitry of the second gas detector increments the indicator of the number of hops or levels of transmission of the alert and includes the incremented indicator with the transmission of the alert to the another gas detector or device, and wherein, in response to receipt of the alert by the second gas detector and/or the another gas detector or device, the data processing circuitry of the second gas detector and/or the another gas detector or device determines whether to provide an alert notification to a user and/or transmit the alert to yet another gas detector or device based on at least one of a determined proximity to the gas detector or device from which the alert was received, a determined duration of time from when the alert was transmitted, a determined severity of the hazardous environmental condition indicated by the alert, or the number of hops or levels of transmission indicated by the indicator included with the alert.

15. A gas detector, comprising:

environmental condition detection circuitry that includes one or more sensors that detect the presence or lack of presence of a particular gas in a vicinity of the gas detector;

data processing circuitry; and wireless communication circuitry, wherein the gas detector is configured to be carried by a user, wherein the environmental condition detection circuitry further includes one or more temperature sensors that detect a temperature in the vicinity of the gas detector and communicates temperature detection data to the data processing circuitry, at least one of the one or more temperature sensors being a biometric sensor configured to detect a body temperature of the user carrying the gas detector and at least one of the one or more temperature sensors detecting an ambient temperature in the vicinity of the gas detector, wherein the data processing circuitry detects a hazardous temperature condition when at least one of a body temperature of the user carrying the gas detector is beyond an upper and/or lower temperature limit or an ambient temperature in the vicinity of the gas detector is beyond an upper and/or lower temperature limit, wherein:

the upper and/or lower temperature limit for the user's body temperature is different than the upper and/or lower temperature limit for the ambient temperature, and the upper and/or lower temperature limit for the ambient temperature depends on the detected body temperature of the user or the upper and/or lower temperature limit for the user's body temperature depends on the detected ambient temperature, and wherein, in response to detection of a hazardous temperature condition, the data processing circuitry of the gas detector provides an alert notification to the user carrying the gas detector.

16. The gas detector of claim 15, wherein a sensory output of the alert notification provided to the user varies depending on an amount of temperature by which the detected body temperature of the user or the ambient temperature is beyond the respective upper and/or lower temperature limit.

17. The gas detector of claim 15, wherein the environmental condition detection circuitry further includes one or more humidity sensors that detect a humidity in the vicinity of the gas detector, and wherein at least one respective upper and/or lower temperature limit varies depending on a magnitude of the detected humidity.

18. A method of communicating an alert in a network of gas detectors in wireless transmission range of one another, each gas detector being configured to be carried by a user and including environmental condition detection circuitry, data processing circuitry, and wireless communication circuitry, the method comprising, by each respective gas detector:

detecting environmental conditions in a vicinity of the respective gas detector, wherein the environmental conditions include a body temperature of the user carrying the respective gas detector and an ambient temperature in the vicinity of the respective gas detector;

communicating detection data based on the detected temperature to the data processing circuitry of the respective gas detector;

detecting a hazardous temperature condition by the respective gas detector in which at least one of a body temperature detected by the respective gas detector is beyond an upper and/or lower temperature limit or an ambient temperature in the vicinity of the respective gas detector is beyond an upper and/or lower temperature limit, wherein the upper and/or lower temperature limit for the body temperature is different than the upper and/or lower temperature limit for the ambient temperature, wherein the upper and/or lower temperature limit for the ambient temperature depends on the detected body temperature or the upper and/or lower temperature limit for the body temperature depends on the detected ambient temperature, and in response to detection of a hazardous temperature condition by the respective gas detector, providing an alert notification to the user carrying the respective gas detector and communicating an alert to one or more other gas detectors in the network of gas detectors via the wireless communication circuitry of the respective gas detector, wherein when communicating the alert to the one or more other gas detectors, the communication includes an indicator of a number of hops or levels of transmission of the alert with the communication, wherein, in response to receipt of the alert from the respective gas detector by the one or more other gas detectors, transmitting the alert from the one or more other gas detectors to yet another gas detector or device via the wireless communication circuitry of the one or more other gas detectors, and wherein, before transmitting the alert from the one or more other gas detectors to said yet another gas detector or device, further incrementing the indicator of the number of hops or levels of transmission of the alert and including the further incremented indicator with the transmission of the alert to said yet another gas detector or device.

19. The method of claim 18, further comprising determining a sensory output of an alert notification provided by the one or more other gas detectors or said yet another gas detector or device based on at least one of:

a determined proximity of the one or more other gas detectors to the respective gas detector that transmitted the alert or a determined proximity of said yet another gas detector or device to the one or more other gas detectors that transmitted the alert, a determined duration of time from when the alert was transmitted, a determined severity of the hazardous temperature condition indicated by the alert, or the number of hops or levels of transmission of the alert indicated by the indicator included with the alert.

20. The method of claim 19, wherein the sensory output of the alert notification is distinct depending on whether the alert is locally generated by the respective gas detector, the one or more other gas detectors, or said yet another gas detector or device, or whether the alert is received from another gas detector.

* * * * *